US011172879B2

(12) United States Patent
Hussain et al.

(10) Patent No.: US 11,172,879 B2
(45) Date of Patent: Nov. 16, 2021

(54) WEARABLE PERSONALIZED MEDICINAL PLATFORM

(71) Applicant: KING ABDULLAH UNIVERSITY OF SCIENCE AND TECHNOLOGY, Thuwal (SA)

(72) Inventors: Muhammad Mustafa Hussain, Austin, TX (US); Abdurrahman Gumus, Istanbul (TR); Wedyan Babatain, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 67 days.

(21) Appl. No.: 16/097,663

(22) PCT Filed: Apr. 26, 2017

(86) PCT No.: PCT/IB2017/052425
§ 371 (c)(1),
(2) Date: Oct. 30, 2018

(87) PCT Pub. No.: WO2017/195060
PCT Pub. Date: Nov. 16, 2017

(65) Prior Publication Data
US 2020/0000403 A1 Jan. 2, 2020

Related U.S. Application Data

(60) Provisional application No. 62/333,492, filed on May 9, 2016.

(51) Int. Cl.
*A61B 5/00* (2006.01)
*G16H 10/60* (2018.01)
(Continued)

(52) U.S. Cl.
CPC ............ *A61B 5/4839* (2013.01); *A61B 5/681* (2013.01); *G16H 10/60* (2018.01); *G16H 20/10* (2018.01);
(Continued)

(58) Field of Classification Search
CPC ... A61B 5/4839; A61B 5/6801; A61B 5/6802; A61B 5/681; A61B 5/68;
(Continued)

(56) References Cited

U.S. PATENT DOCUMENTS 6,471,087 B1 * 10/2002 Shusterman ....... A61B 5/02055
221/2
2004/0121486 A1 6/2004 Uhland et al.
(Continued)

OTHER PUBLICATIONS

Roxhed, Niclas, et al. "A compact, low-cost microliter-range liquid dispenser based on expandable microspheres." Journal of Micromechanics and Microengineering 16.12 (2006): 2740. (Year: 2006).*
(Continued)

*Primary Examiner* — Nilay J Shah
(74) *Attorney, Agent, or Firm* — Patent Portfolio Builders PLLC

(57) ABSTRACT

An apparatus for personal health maintenance has a sensor attached at least indirectly to a carrier member in turn attachable to a user or subject and configured for measurement of at least one physiological parameter of the user. A reservoir contains a preselected composition. An electronic processor is operatively connected to the sensor for receiving a signal therefrom encoding a measurement of the physiological parameter, the processor being configured for determining a divergence of the physiological parameter from a predetermined magnitude, the processor being operatively connected to a dispensing mechanism for ejecting, from the reservoir, an amount of the composition to be administered to the user to reduce divergence of the physi-
(Continued)

ological parameter from the predetermined magnitude. The dispensing mechanism includes an expandable polymer composite layer with gas-filled micro-bubbles or microspheres expandable by operation of a heating element.

19 Claims, 13 Drawing Sheets

(51) Int. Cl.
   *G16H 20/10* (2018.01)
   *A61M 5/172* (2006.01)
   *A61M 5/145* (2006.01)
   *A61M 5/155* (2006.01)
(52) U.S. Cl.
   CPC .......... *A61B 5/683* (2013.01); *A61B 2562/028* (2013.01); *A61M 5/14593* (2013.01); *A61M 5/155* (2013.01); *A61M 5/1723* (2013.01)
(58) Field of Classification Search
   CPC .......... A61B 2562/028; A61M 5/1723; A61M 2005/1726; A61M 5/155; A61M 5/145; A61M 5/142; A61M 2005/14204; G16H 20/10; G16H 10/10; G16H 20/13; G16H 20/17; G16H 20/60; G16H 20/70; G16H 20/90
   See application file for complete search history.

(56) References Cited

U.S. PATENT DOCUMENTS

| | | | |
|---|---|---|---|
| 2005/0043894 A1* | 2/2005 | Fernandez | G16B 5/00 702/19 |
| 2005/0277912 A1* | 12/2005 | John | A61M 25/0097 604/890.1 |
| 2008/0154179 A1* | 6/2008 | Cantor | A61M 37/00 604/20 |
| 2016/0029962 A1* | 2/2016 | Hyde | G16H 40/63 600/301 |
| 2016/0066828 A1 | 3/2016 | Phan et al. | |

OTHER PUBLICATIONS

Abrahams, E., et al.; "The Case for Personalized Medicine."; J. Diabetes Sci. Technol, vol. 3, Issue 4; Jul. 4, 2009; pp. 680-684.
Adamo, A., et al.; "On-demand continuous-flow production of pharmaceuticals in a compact, reconfigurable system"; Science vol. 352, Issue 6281, Apr. 1, 2016; pp. 61-67.
Chan, I., et al.; "Personalized Medicine: Progress and Promise"; Annu. Rev. Genomics Hum. Genet. 12; Jun. 29, 2011; pp. 217-244.
Choi, et al.; "Cephalopod-Inspired Miniaturized Suction Cups for Smart Medical Skin"; Adv. Healthcare Mat. 5; May 20, 2015; pp. 80-87.
Erickson, D., et al.; "Smartphone technology can be transformative to the deployment of lab on-chip diagnostics"; Lab Chip 14; Mar. 25, 2014; pp. 3159-3164.
Farra, R., et al.; "First-In-Human Testing of a Wirelessly Controlled Drug Delivery Microchip"; Sci. Transl. Med., vol. 4, Issue 122; Feb. 22, 2012, 12 pages.
Gao, W. et al.; "Fully integrated wearable sensor arrays for multiplexed in situ perspiration analysis"; Nature 509, vol. 529, Jan. 28, 2016; pp. 509-514.

Honda, W., et al.; "Wearable, Human-Interactive, Health-Monitoring, Wireless Devices Fabricated by Macroscale Printing Techniques"; Adv.Functional Mat. 24; Feb. 28, 2014; pp. 3299-3304.
Jeong,, J.-W., et al.; "Wireless Optofluidic Systems for Programmable In Vivo Pharmacology and Optogenetics"; Cell 162; Jul. 30, 2015; pp. 662-674.
Kim, D.-H. et al.; "Epidermal Electronics"; Science vol. 333; Aug. 12, 2011; pp. 838-843.
Lee, C. H., et al.; "Materials and Wireless Microfluidic Systems for Electronics Capable of Chemical Dissolution on Demand"; Adv Funct. Mat. 25; Dec. 23, 2014; pp. 1338-1343.
Monsen, E. R.; "Dietary reference intakes for the antioxidant nutrients: vitamin C, vitamin E, selenium, and carotenoids"; Journal of the American Dietetic Association 100; Sep. 2000; pp. 637-640.
Mudanyali, O., et al.; "Integrated rapid-diagnostic-test reader platform on a cellphone"; Lab Chip 12, Apr. 16, 2012; pp. 2678-2686.
Nassar, J. M., et al.; "Paper Skin Multisensory Platform for Simultaneous Environmental Monitoring"; Adv. Materials Tech.; Feb. 19, 2016, 14 pages.
National Academy Press; "Dietary reference intakes for thiamin, riboflavin, niacin, vitamin B6, folate, vitamin B12, pantothenic acid, biotin, and choline"; (National Academies Press (US), 1998; 592 pages. (Publication month unavailable—Per 37 CFR 1.98(b) The year of publication is sufficiently earlier than the effective U.S. filing date and any foreign priority date so that the particular month of publication is not in issue.).
Oncescu, V., et al.; Cholesterol testing on a smartphone. Lab Chip 14; Nov. 28, 2013; pp. 759-763.
Oncescu, V., et al.; "Smartphone based health accessory for colorimetric detection of biomarkers in sweat and saliva"; Lab on a Chip 13, Jun. 7, 2013; pp. 3232-3238.
Ozcan, A.; "Mobile phones democratize and cultivate next-generation imaging, diagnostics and measurement tools"; Lab on a Chip 14; Feb. 12, 2014; pp. 3187-3194.
Roxhed, N. et al.; "A compact, low-cost microliter-range liquid dispenser based on expandable microspheres"; J. Microelectromech. Syst. 16; Nov. 17, 2006; pp. 2740-2746.
Samel, B., et al.; "A Thermally Responsive PDMS Composite and Its Microfluidic Applications"; J. Microelectromech. Syst., vol. 16, No. 1; Feb. 2007; pp. 50-57.
Schwartz. G., et al.; "Flexible polymer transistors with high pressure sensitivity for application in electronic skin and health monitoring"; Nat. Commun. 4:1859; May 14, 2013; 8 pages.
Spear, B., et al.; Clinical application of pharmacogenetics. Trends Mol. Med. vol. 7, No. 5; May 2001; pp. 201-204.
Spieth, S., et al.; "An intra-cerebral drug delivery system for freely moving animals"; Biomed. Microdevices 14; May 24, 2012; pp. 799-809.
Trumbo, P., et al.; "Dietary reference intakes: vitamin A, vitamin K, arsenic, boron, chromium, copper, iodine, iron, manganese, molybdenum, nickel, silicon, vanadium, and zinc"; J. Am. Diet. Assoc., vol. 101, No. 3; Mar. 2001, pp. 294-301.
International Search Report in related International Application No. PCT/IB2017/052425, dated Jul. 25, 2017.
Jeong, J.-W., et al., "Wireless Optofluidic Systems for Programmable In Vivo Pharmacology and Optogenetics," Cell, Jul. 30, 2015, vol. 162, pp. 662-674.
Written Opinion of the International Searching Authority in related International Application No. PCT/IB2017/052425, dated Jul. 25, 2017.

\* cited by examiner

WEARABLE PERSONALIZED MEDICINAL PLATFORM

CROSS-REFERENCE TO RELATED APPLICATIONS

This application is a U.S. National Stage Application of International Application No. PCT/IB2017/052425, filed on Apr. 26, 2017, which claims priority and benefit from U.S. Provisional Patent Application No. 62/333,492, filed May 9, 2016, the entire contents of which are incorporated herein by reference.

The present invention is directed to a wearable apparatus for personal health maintenance. The present invention may be embodied as a wearable personalized medicinal platform.

Healthcare today is focused largely on "one size fits all" treatments. Patients with similar medical issues can be given the same medication and dosage, but the treatment might not be effective for all of them[1-3]. There is an emerging field called as personalized medicine, which can be considered as going beyond the traditional approaches to understand and treat diseases. Personalization of the medication gives physicians the ability to use the patient's mainly genetic information to guide selection of certain drugs or treatments for individuals, which can increase the possibility of a more effective and low cost approach for clinical care[1,2]. Recently, researchers developed a compact, reconfigurable manufacturing platform which can produce pharmaceuticals on-demand, continuously for small quantities with shorter processing times which could be helpful to produce personalized medicines in the future more easily[4].

Technological advances such as lab-on-a-chip technologies have enabled the deployment of easy to use, disposable, and informative diagnostic tests directly to the consumer allowing them to take control of their own health[5-7]. There are also wearable sensor technologies developed to pursue personalized clinical investigations through real-time continuous physiological monitoring of an individual[8-11].

Smartphone technology is rapidly being more accessible and a potentially transformative opportunity for the deployment of these health monitoring technologies with its communication and computational capabilities[6]. Since most consumers already own a test reader/instrument in the form of a smart phone, integration of existing rapid diagnostic test strips or wearable health sensors to smartphones is an emerging research field[5,7,12]. On the other hand, more complex devices are being developed for the analysis of blood which can give a wealth of information ranging from general molecular markers of infectious diseases, to cancer diagnostics, genetic analysis, vitamins and micronutrient deficiencies[13]. This can increase the awareness through physiological feedback by enabling rapid detection of body vitals and molecular signs which could potentially decrease many health problems. Wearable sensor technologies will record the data for certain intervals and be integrated with smart phones where they can remind the user about his/her condition. Alternatively, a smart phone can send results to the doctor which can save time and effort for both doctors and patients.

This also enables doctors to intervene remotely through drug delivery devices or schedule an appointment with a patient. These medical monitoring and drug delivery devices[7-10] decrease the cost of healthcare and increase the quality of life of patients. Significant work has been done previously using similar device structures to the system presented here to apply different dosages of a drug[14], applying single dosage of different drugs[15], or microfluidic platform that can integrate active dosing[16]. Still using these devices for the personalization of medicine and incorporating them for appropriate applications is yet to be done.

SUMMARY OF THE INVENTION

To complement as well as to significantly advance the earlier works, here we show a wearable personalized medicinal platform that has the capability to prepare (vary and mix multiple constituents) drugs, vitamins, and minerals on demand or depending on the needs of the individual using integrated wearable health sensors. By integrating with advance complementary metal oxide semiconductor (CMOS) electronics and technology, we present this microfluidics-based wearable medicinal preparation platform to pursue the goal of the in-situ personalization of medicine preparation which offers a unique impact on global healthcare. Instead of "one size fits all" treatment approaches for healthcare issues, the demonstrated system can prepare the drugs, vitamins and minerals instantly and in-situ depending on the needs of a person at any given time.

The system developed here has the capability of mixing two (can be scaled up further in straight forward manner) different drugs with different dosages on demand or with external stimuli through wearable body sensors when it is tested on a human subject.

Adaptive drug preparation is critical to personalize healthcare and immediate application areas are energy drinks and multi-vitamins for everyone and specially soldiers, athletes, patients and blue collar personnel.

An apparatus for personal health maintenance comprises, in accordance with the present invention, a carrier member, at least one sensor attached at least indirectly to the carrier member and configured for measurement of at least one physiological parameter of a user, an attachment device connected to the carrier member for maintaining the sensor in operative proximity with the user, at least one reservoir provided on the carrier member and containing a preselected composition, a dispensing mechanism provided on the carrier member in operative contact with the reservoir, and an electronic processor mounted to or carried by the carrier member and operatively connected to the sensor for receiving a signal therefrom encoding a measurement of the physiological parameter. The processor is configured for determining a divergence of the physiological parameter from a predetermined magnitude an is operatively connected to the dispensing mechanism for operating the same to eject, from the reservoir, an amount of the composition to be administered to the user to reduce divergence of the physiological parameter from the predetermined magnitude.

The dispensing mechanism preferably includes an expandable polymer composite layer. The expandable polymer composite layer preferably includes gas-filled microbubbles or microspheres. The dispensing mechanism preferably further includes an electric circuit with at least one heating element proximate the expandable polymer composite layer.

Thus, in an apparatus in accordance with the present invention, the reservoir is part of a microfluidic circuit disposed on a substrate included in the carrier member.

The sensor is preferably configured for non-invasive detection of the physiological parameter. The physiological parameter may be body temperature, blood pressure, pulse rate, skin hydration, perspiration state, respiration rate, glucose level, and oxygen content. When multiple sensors are provided, each may measure a different one of these physiological parameters. Concomitantly, the sensor may be a temperature sensor, an electrical conductivity or electrical resistance detector, a pressure sensor, a moisture sensor, etc.

The physiological parameter may be a level of an analyte such as calcium, potassium, magnesium, and glucose or a pharmaceutical analyte. Alternatively, the physiological parameter may be a physiological abnormality such as acute myocardial infarction, subarachnoid bleed, and fluid accumulation around the heart.

In one embodiment of the invention, the dispensing mechanism includes a nozzle to dispense the amount of the composition into or onto an ingestible substance. The user may be alerted to the recommended supplement by operation of an alert signal generator operatively connected to the processor for prompting the user to take action to ingest the amount of the composition.

The composition in the reservoir may include one or more vitamins.

It is to be noted that multiple reservoirs may be provided in the apparatus, each containing a predetermined amount of a preselected composition. A respective, dedicated heating element for each such reservoir is included in the electrical circuit.

The multiple reservoir may contain different compositions, thus enabling mixing of different composite compositions depending on the needs of the user as determined by multiple sensor readings and the pre-programmed processor.

A microfluidic dispensing assembly in accordance with the present invention comprises a substrate, at least one reservoir provided on the substrate and containing a preselected composition, and a dispensing mechanism provided in juxtaposition to the at least one reservoir, where the dispensing mechanism includes an expandable polymer composite layer. The microfluidic dispensing assembly further comprises an electronic processor operatively connected to the dispensing mechanism for operating the same to eject, from the reservoir, an amount of the composition.

Pursuant to one feature of the present invention, the expandable polymer composite layer includes gas-filled micro-bubbles or microspheres. The dispensing mechanism further includes an electric circuit with at least one heating element proximate the expandable polymer composite layer, the processor being operatively connected to the electric circuit.

The reservoir is part of a microfluidic circuit disposed on the substrate.

A sensor may operatively connected to the processor and attachment means for maintaining the sensor in operative engagement with a user. In that case, the processor is configured for receiving a signal from the sensor encoding a measurement of a physiological parameter, the processor being further configured for determining a divergence of the physiological parameter from a predetermined magnitude. The processor is operatively connected to the dispensing mechanism for operating the same to eject, from the reservoir, an amount of the composition to be administered to the user to reduce divergence of the physiological parameter from the predetermined magnitude.

BRIEF DESCRIPTION OF THE DRAWINGS

FIG. 4a also includes two photographs of an experimental wearable personalized medical system attached to an arm of a test subject.

DETAILED DESCRIPTION

Figure 1:
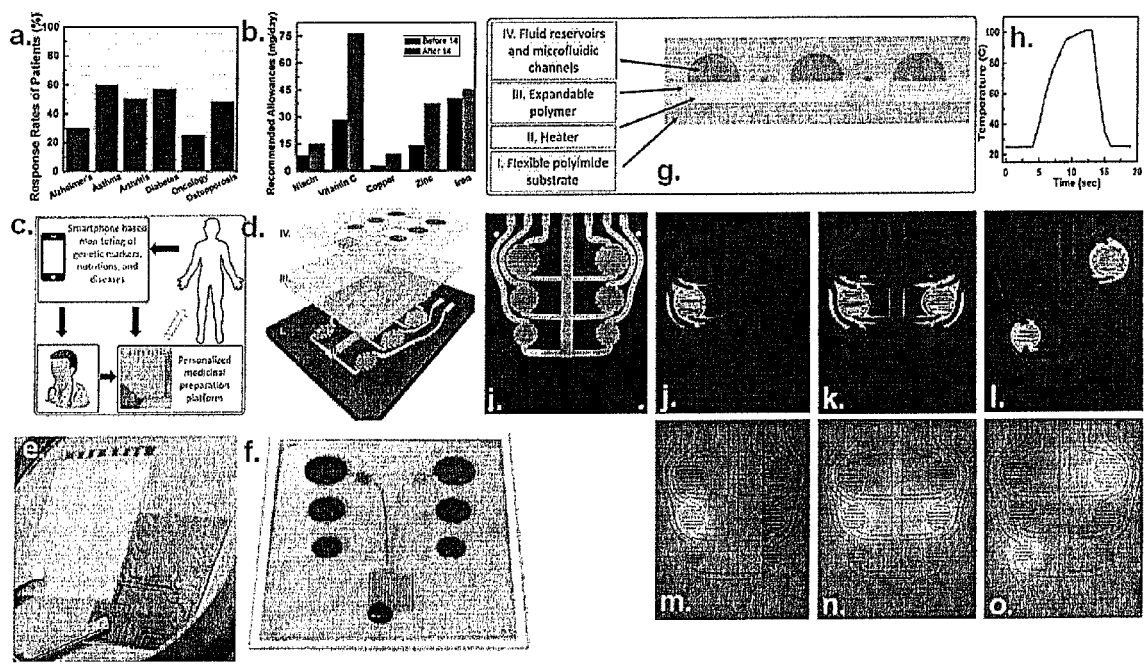
FIG. 1a is a graph showing response rates of patients to medications for different diseases[2].
FIG. 1b is a graph showing different vitamin and mineral needs of people below and after 14 years age[17-19].
FIG. 1c is a diagram illustrating operation principle of a web integrated wearable personalized medical system in accordance with the present invention.
FIG. 1d is a schematic exploded perspective view of selected parts of a wearable personalized medical system in accordance with the present invention, including, top to bottom, a microfluidic system, an expandable polymer composite layer and electric heaters.
FIG. 1e is a photograph showing components of an advanced version of a wearable personalized medical system pursuant to the present invention, with flexible silicon CMOS chip sets (25 μm thick, 1 $mm^2$ with 256 fan-outs in a spider-web) on the back (imaged using a mirror).
FIG. 1f is a schematic isometric top and front view of a fully functional medicinal platform in accordance with the present invention, with two different liquids (red and green colored in a color version of the figure) contained in different sizes of reservoir.
FIG. 1g is a schematic cross-sectional view of a wearable personalized medical system pursuant to the present invention.
FIG. 1h is a photograph showing an electric circuit and reservoirs of a wearable personalized medical system in accordance with the invention, showing experimental results of electrode temperature increase and decrease profiles.
FIGS. 1i through 1l are infrared photographs of an electric circuit of a wearable personalized medical system in accordance with the invention, depicting thermal actuator electrodes powered up sequentially and infrared (IR) images were collected to observe the temperature profiles and distributions.
FIG. 1m through 1o are infrared photographs of an electric circuit of a wearable personalized medical system in accordance with the invention showing an investigation of temperature profiles with Finite Element Analysis (FEA).

As can be seen from FIGS. 1a-1b, for some of the most common diseases, drugs on the market work only for a percentage (at the most 60%) of the population[2] and for multi-vitamins—personalization can be more effective[17-19], respectively. Patients continue to switch from one drug to another until they find an effective therapy. This increases the cost of the medical treatment while compromising the quality of life and life expectancy of the patients[1]. Rather than trial-and-error prescriptions, technological developments have enabled us to understand human genetics and its influence on disease and treatment, allowing physicians to select the optimal therapy during early stages of treatment[3]. As portable personal genome sequencers are imminent, by incorporating personal genome sequencers with smartphones' computation and communication capabilities, we have the ability to do not just one time analysis of genetic markers, but continuous tracking of the changes on our genetic signatures throughout our life. By combining this genetic information with other physiological data acquired by wearable sensors, it is possible to evaluate a person's susceptibility to diseases and health condition continuously and address it accordingly. Personalized medicinal platform will play an increasingly critical role with the ability of preparing different drugs at different dosages autonomously or on demand precisely and safely (FIG. 1c). This also creates a new opportunity for the personalization of vitamin and mineral supplements where each person gets the amount of nutrient one needs, which can vary with multitude of variables (FIG. 1b).

FIGS. 1d-1g show the details of the device structure and the system itself with varying degrees of maturity. Laser-patterning of electrodes enabled etching the sputtered gold easily up to a resolution of 100 μm (FIG. 1i). Polyimide sheet (125 μm thick) was chosen as a substrate with low thermal conductivity (0.46 W m-1 K) which can reach high temperatures (>90° C.) without thermal noise between electrodes. Using a thin polyimide sheet as a substrate also gives advantage of flexibility for flexible microfluidic applications in various versions of the medicinal platform. Each electrode is individually addressable.

FIGS. 1j-1l shows sequential activation of heating electrodes through thermal mapping collected with an IR camera. Power was delivered to the system using a coin cell battery (CR2032 Lithium Coin Cell Battery with 20 mm diameter, 0.02 lb shipping weights, 3 volts voltage and 200 mAh capacity) for joule heating over 90° C. within ~10 seconds of triggering. Temperature dissipates only around the triggered electrode avoiding any thermal cross talk between electrodes and allowing independent operation of each reservoir. After release of the trigger, temperature decreases to room temperature within four seconds (FIG. 1h). Temperature profiling results agree with Finite Elemental Analysis (FEA) using COMSOL™ Multiphysics (110 FIGS. 1m-o). Simulation details can be found in the Supplementary Information (SI) section below.

We preferred to use a solid microfluidic channels (PMMA) (FIG. S1) with low moisture and water absorbing capacity. The Computer Numerical Control (CNC) based direct micro-milling process to pattern microfluidic channels used here, can be easily implemented in any high-precision CNC machine without a need for a clean room facility. The LPKF™ system has an x-y resolution of ±0.5 μm and is equipped with a depth delimiter that reduces the depth variation across the chip below ±10 μm, depending on the substrate flatness. Channels have a negligible surface roughness (~150 nm) which was validated with a profilometer. Incorporating different layers of the system using double sided tape enables an inexpensive and simple device assembly enabling the concept of Do It Yourself (DIY).

Each reservoir connects to a microfluidic mixing chamber. Infusion of the fluids into the mixing chamber from the reservoirs is initiated through expansion of the expandable polymeric material induced by joule heating of one or more underlying heating electrodes[14-16,20]. The active layer increases its volume by thermal expansion of expandable microspheres that encapsulate hydrocarbon gas (FIGS. 2a-2d). The expandable polymer composite undergoes a rapid and irreversible change in volume around 7 times at ~80° C. (FIG. 2d), which pushes the liquid out of the reservoirs towards microfluidic channels. For future versions of the device, it is possible to avoid water absorption of PDMS/Expancel mixture by coating with a thin (5 μm) layer of parlyene. This is helpful in applications where it might be necessary to store the drugs for long term.

Figure 2:
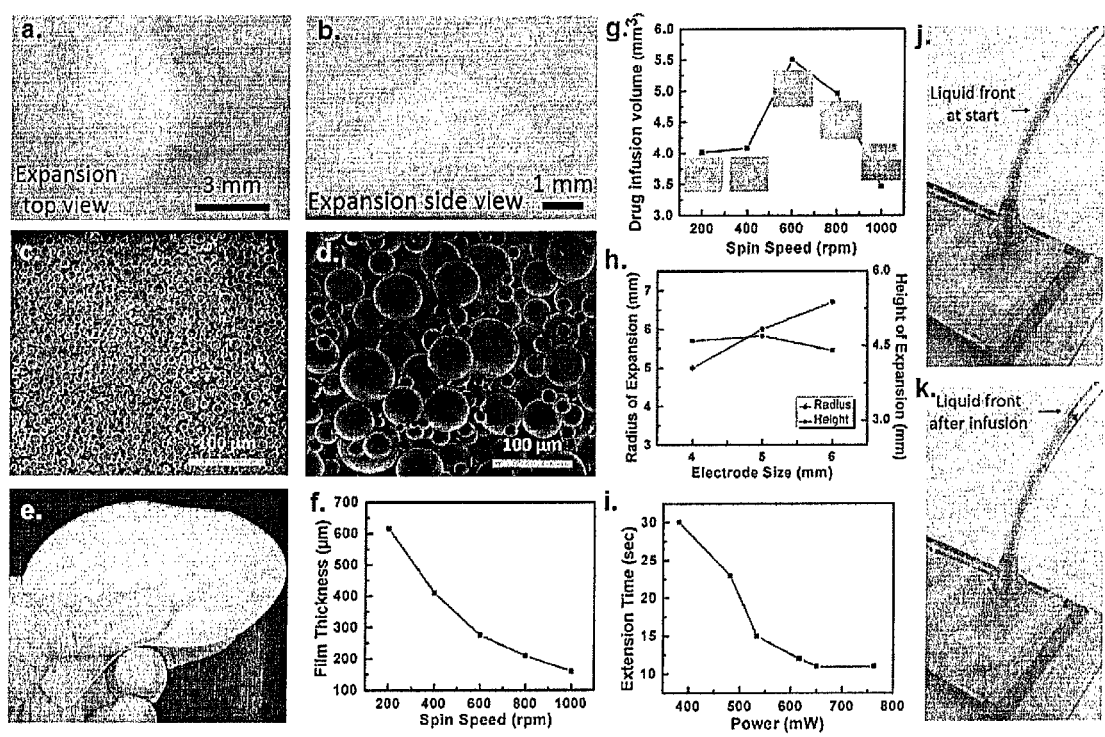
FIGS. 2a and 2b are photographs of an expandable polymer layer of a wearable personalized medical system in accordance with the invention, after expansion thereof.
FIGS. 2c and 2d are SEM images of expandable polymer particles composite incorporated into a wearable personalized medical system in accordance with the invention.
FIG. 2e is a photograph of am expandable polymer layer after release from a 4-inch wafer.
FIG. 2f is a graph of film thickness as a function of spin speed in the manufacture of an expandable polymer composite layer for incorporation in a wearable personalized medical system in accordance with the invention.
FIG. 2g is a graph of drug infusion volume as a function of spin coating speed in the manufacture of an expandable polymer composite layer for incorporation in a wearable personalized medical system in accordance with the invention.
FIG. 2h is a graph of radius and height of expansion of gas-filled microspheres as functions of different electrode size, in a wearable personalized medical system in accordance with the invention.
FIG. 2i is a graph of extension time as a function of power input to the electrodes.
FIGS. 2j and 2k are photographs of a drug infusion test setup showing liquid places marked before and after infusion.

Thickness of the expandable polymer layer can be altered by changing the spin coating speed (FIG. 2D, which affects the infused volume of drugs from the reservoirs. We have found an optimum thickness value around 600 rpm (~275 μm), where most of the drug was discharged from the reservoirs (FIGS. 2f-2g). Thinner or thicker expandable composite layers in comparison to 600 rpm cannot eject all of the fluid. Radius of the expansion linearly changes with electrode sizes (FIG. 2h). On the other hand, height of the expanded composite does not change with electrode sizes.

Extension time of the expandable composite is another important parameter during drug infusion. We have investigated extension time for different power inputs, and found out that ideal power values are 500-600 mW to get an extension between 10 to 15 seconds (FIG. 2i). FIGS. 2j-2k show photographs of drug infusion test setup showing liquid places marked before and after infusion.

Figure 3A:
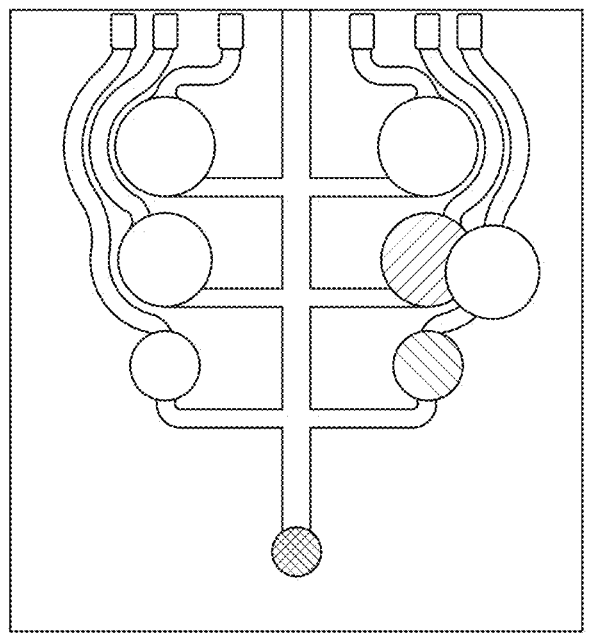
FIG. 3a through 3f are optical images of a set of reservoirs of a wearable personalized medical system in accordance with the invention, showing selective triggering or personalized medicinal preparation platform where reservoirs filled with water solutions (different colors and different pH values) to get a desired output mixture.
Figure 3B:
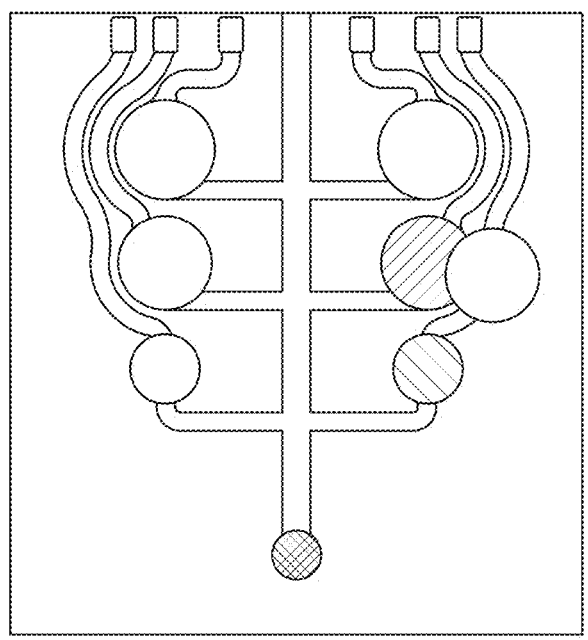
Figure 3C:
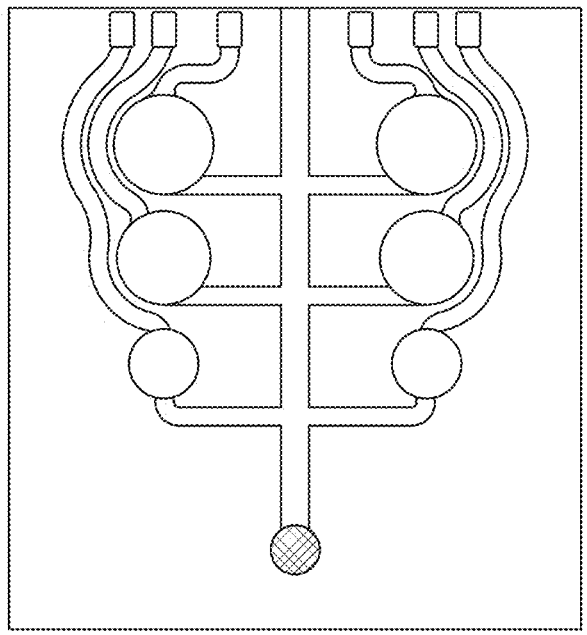
Figure 3D:
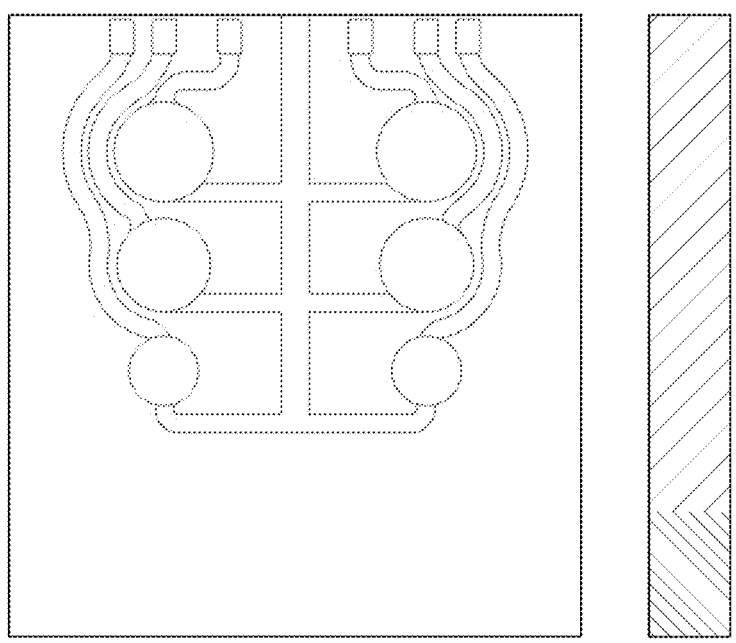
Figure 3E:
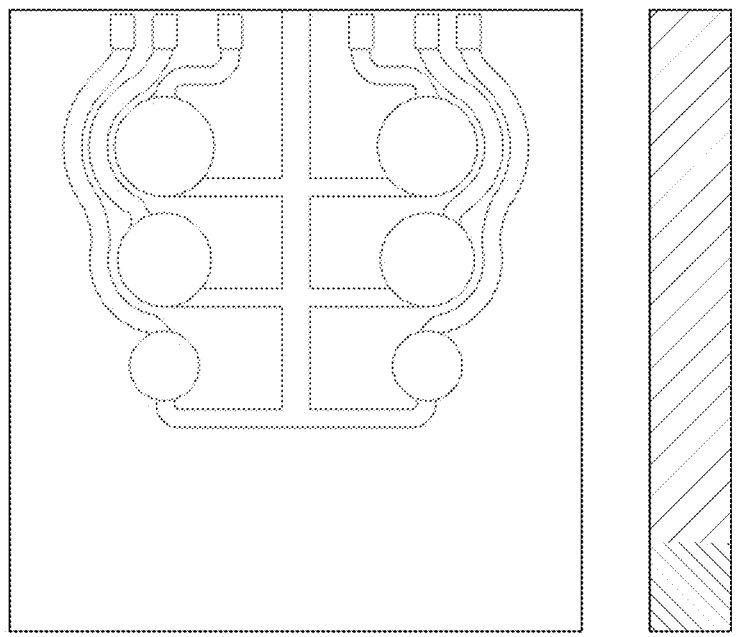
Figure 3F:
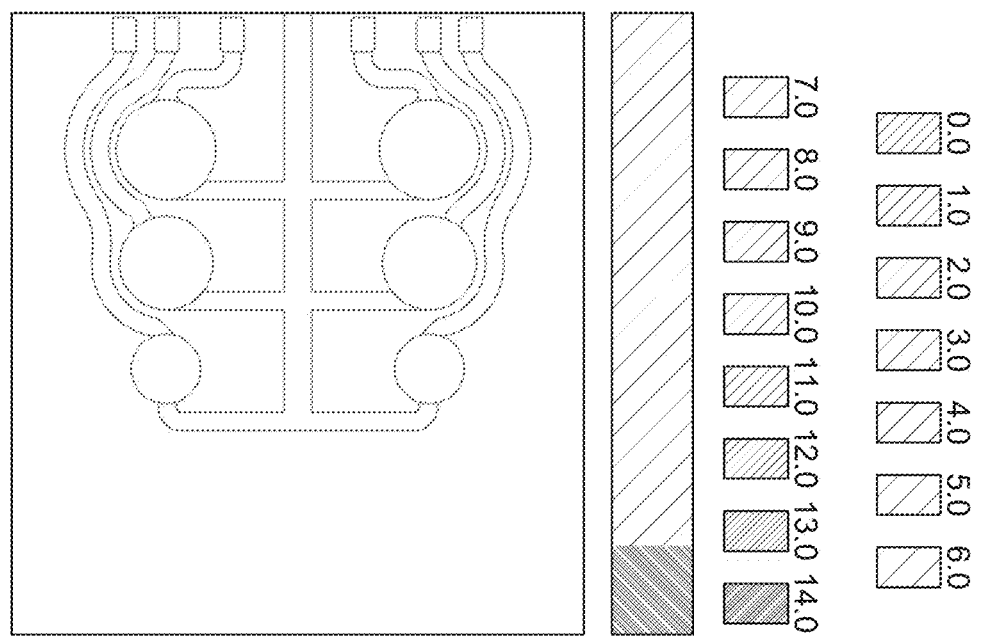
Figure 3G:
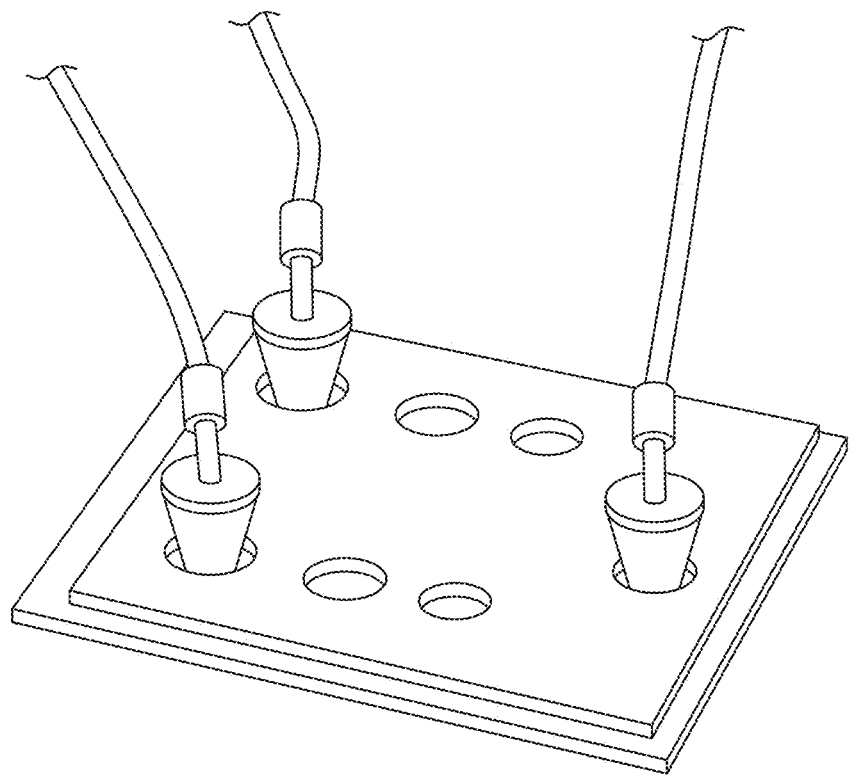
FIG. 3g is a photograph an experimental set-up in validation of microfluidic mixing capability of a wearable personalized medical system in accordance with the invention (yellow and blue liquid mixture yielding a green colored liquid).

The device consists of different sizes of drug chambers to keep different amounts and types of drugs. For demonstration purposes, we used food dye colored water as a solution. As shown in FIGS. 3a-3c, by selectively enabling different drug reservoirs of personalized medicinal platform, we were able to eject the solution out of the device. Initially individual reservoirs were enabled to eject blue and yellow solutions separately and then mixed different colors of solutions (blue and yellow) to form a desired mixture output (green) (FIG. 3a-3c). We also investigated the system's capability with different pH value solutions and changing the output solution's pH by triggering different reservoirs (FIG. 3d-3f). The envisioned function here is the controlled release of drugs with different dosages and mixture upon the need. FIG. 3g demonstrates the mixing ability of the microfluidic channels. Blue and yellow solutions enter the personalized medicinal platform's microfluidic channels at a constant speed (5 µl/min) using a syringe pump and resulting in a green solution at the output channel.

Figure 3H:
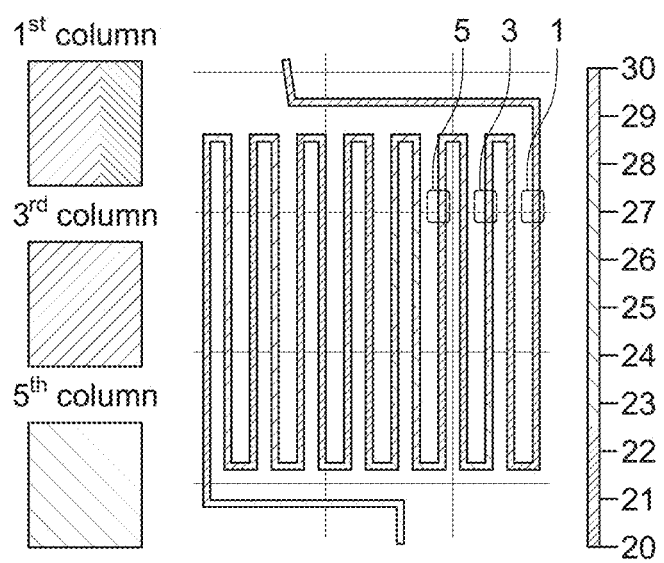
FIG. 3h is a 3D FEA to observe the simultaneous flow of liquids through a micromixer channel structure in accordance with the invention.
Figure 3I:
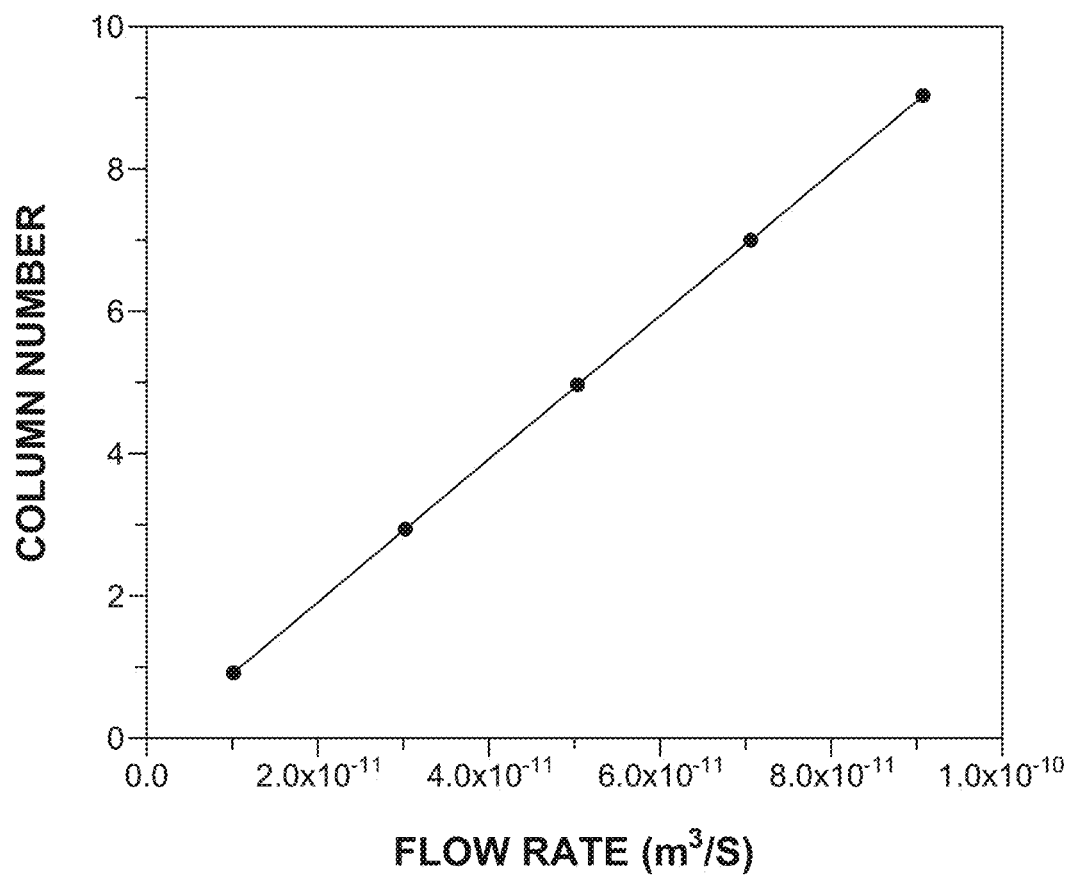
FIG. 3i is a graph of column number as a function of flow rate of solution mixing using FAE.

We have also investigated the effect of viscosity change of the fluids to the mixture output through simulations, and found out viscosity changes of the solutions (up to 30%) do not affect the mixture of the drugs (data not shown). A 3D FEA was carried out to observe the simultaneous flow of liquids through the micromixer structure of the channels. The simulation result for the stationary study of the concentration plot is shown in FIG. 3h. It can be observed that the two liquids are completely mixed around 6th column of the mixer. Moreover, we have varied the flow rate at the input of the channels and observed the complete mixing of fluids at different column numbers, as shown in FIG. 3i. It can be observed that as the flow rate is increased, the complete mixing of fluids occurs at higher column numbers.

A personalized medicinal platform as described herein can operate not only by user activated schemes, but in different modes such as autonomous triggering in response to sensors measuring body vitals or smartphone based operation. We have already shown in FIG. 1c the envisioned working schematic of the system. Vital signs such as, heart rate, blood pressure, body temperature, skin hydration, sweat condition and respiration rate, give important information about the physiological status of the human body8, 10,21-23. Genetic markers, nutrition and diseases can be detected using lab-on-a-chip based technologies. If there is a need for urgent medical attention, the output of the system can be broadcasted to emergency medical providers for required intervention.

Figure 4A:
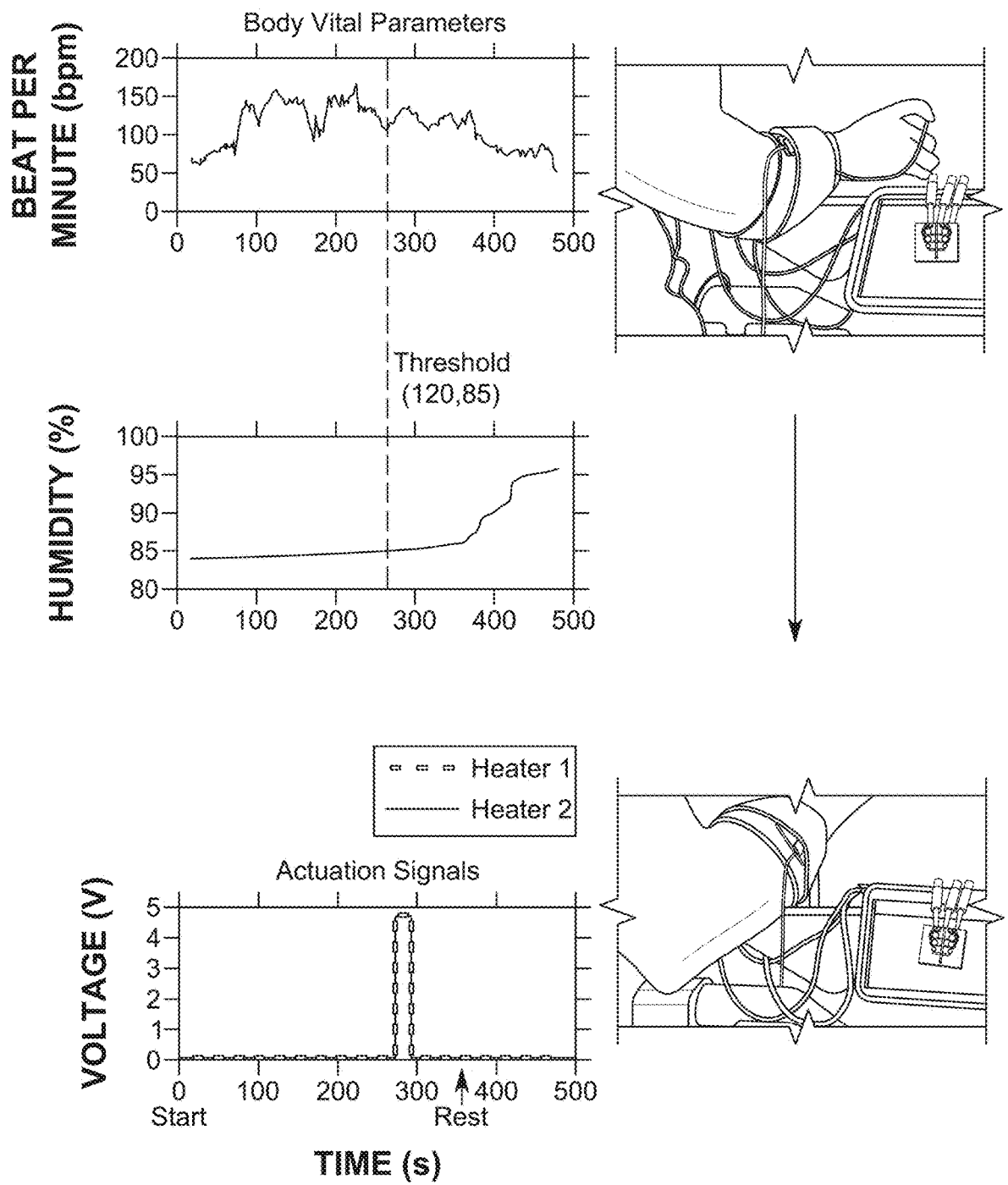
FIG. 4a is a set of three graphs of physiological parameters detectable via skin sensors, pulse rate, humidity, and electric potential medicinal platform by triggering the device after detecting physical fatigue from wearable sensors.
Figure 4B:
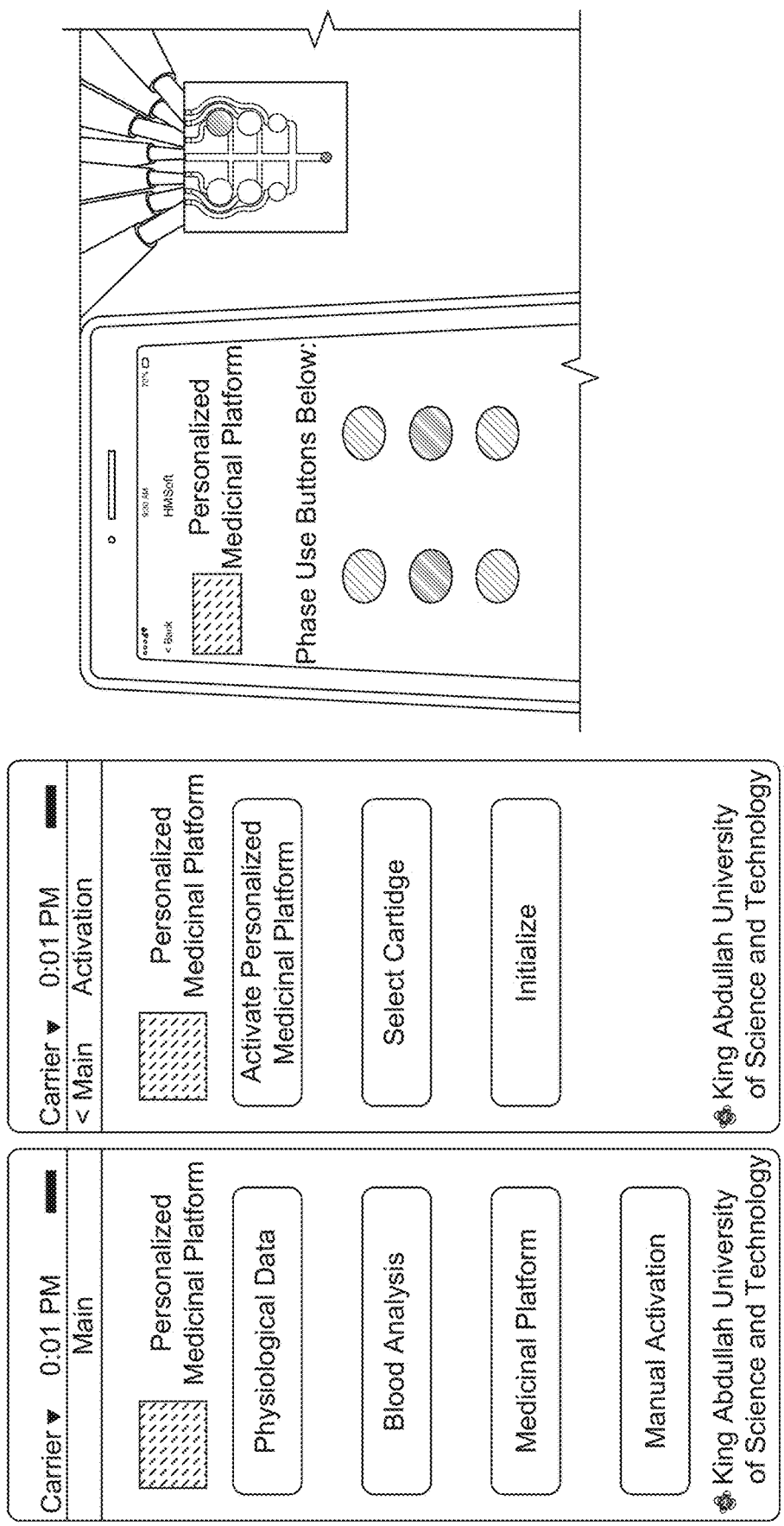
FIG. 4b are Web screenshots of a developed App from an iPhone display (left) and a smartphone-based wireless operation of medicinal platform (right).

FIG. 4a demonstrates an example application of the proposed medicinal platform by detecting physical fatigue via wearable sensors. Details of the integrated system can be found at in the Supplementary Information below (including FIGS. S1-S2). CMOS based heart rate and humidity sensors are interfaced with the medicinal platform 177 integrated system and applied to the subject's skin as shown in FIG. S2. In the data shown here, the subject performs an 8-minute test including constant running on a treadmill at 12 mph. As the subject's beat-per minute and skin moisture both reach a certain threshold (120 bpm, 85% RH) the system actuates the medicinal platform triggering a mixing process between two different fluid reservoirs as documented in Supplementary Video S1. The resulting liquid could then be injected to the subject; for instance, to compensate for a deficiency in certain concentration of body vitamins or minerals. This responsive medicinal platform will open up new possibilities of real-time, efficient, and low-cost drug preparation and delivery without human interaction based on physiological data and can be used in a broad range of healthcare applications. In FIG. 4b, we have demonstrated a smartphone based control of the medicinal preparation platform where individual reservoirs are triggered using an App and desired drug output achieved. This smartphone App can be further developed to achieve analysis of physiological and blood analysis data and take a required action autonomously.

One of the limitations of the above-described version of the device is to have remaining fluids inside the microfluidic channels after infusion which can get mixed with the drug coming afterwards. To overcome this challenge, more complicated microfluidic systems are provided with a self-cleaning capability where fluidic pressure, exemplarily from saline solution stored in one or more dedicated cleaning reservoirs, push the remaining fluid out of the channels and then infuse a new set of drugs. On the other hand, this is not a problem for applications where drug mixing is contemplated. One time usage of each reservoir is another disadvantage of the above-described embodiment. To overcome this challenge, more complex pumping mechanisms ar incorporated to push fluids out of the reservoirs stepwise. One option is a reusable personalized medicinal platform serving as a replaceable cartridge which can be easily changed for different drug/vitamin needs. Additionally, the number of reservoirs can be increased to improve the systems capability. We also envision a DIY version of the whole system using recyclable materials for further affordability.

Methods: Fabrication of Personalized Medicinal Platform

Device design details are shown schematically in FIGS. 1d-1g. 185 nm gold was sputtered on 125 µm thick polyimide film (Good Fellows) and electrodes were patterned using 1.06 µm ytterbium-doped fiber laser (PLS6MW Multi-Wavelength Laser Platform, Universal Laser Systems) (FIG. 1h). Thermally expandable polymer (Expancel, 031 DU 40, AkzoNobel) was mixed with polydimethylsiloxane (PDMS) (2:1 ratio) and spin coated on wafer to get a thin (~275 µm) sheet of expandable polymer composite and cured in an oven at 65° C. for 2 hours. It was then peeled off from the wafer using razor blade to get a thin layer of expandable polymer composite which was then placed on heating electrodes using double sided adhesive film (30 µm thick, ARclear, Adhesive Research). Thermal maps of activated heating electrodes were collected with an infrared (IR) camera (FIG. 1j) where the speed of heating and cooling was also analyzed (FIG. 1k). Temperature profiles were also investigated with finite element analysis using COMSOL Multiphysics (FIG. 1l). Microfluidic channels and drug reservoirs are made of 1 mm sheet of poly(methylmethacrylate) PMMA, an inexpensive material commonly used in microfluidics. Microfluidic channels (~150 µm width and ~100 µm deep) and reservoirs are directly micromachined on PMMA using a printed circuit board plotter (LPKF Protomat S103). Three different reservoir sizes (6.3 mm3, 9.8 mm3, 14.1 mm3) were fabricated to get different amounts of drug infusions. Surface roughness of the channels were measured with a profilometer (Ambios XP-200, Ambios Technology). After micromachining process, the device was brushed with soapy water, rinsed with ethanol, blown dry with compressed air and visually inspected to guarantee that no residue left from the milling process which might block the channels. Double sided tape is used to assemble the heating electrodes, expandable polymer layer, and microfluidic channels/reservoirs to each other. reservoirs were filled with water dyed with food color through predefined holes (~0.4 mm diameter) and then sealed with transparent, water-proof tape (3M Corporation).

Methods: Expandable Polymer Composite Characterization

Thermally expandable polymers have been previously used by several research groups to manipulate the fluids inside microfluidics systems14-16,20,25. The thermally expandable polymer consists of small microspheres which encapsulates a gas, where its internal pressure increases upon heating and its size increases around 7 times more (FIGS. 2a-2c). This causes the expandable composite to increase in size towards the reservoir area and pushes the loaded fluid towards the microfluidic channels. Spin coating speed of the composite determines the thickness of the film (FIG. 2d). We investigated the thickness change effect on the drug infusion ratio (FIGS. 2e-2f) and the size of expansion for different electrode sizes (FIG. 2g). Extension time was also investigated for different power inputs (FIG. 2h).

Methods: Operation of the Device

We used thermally expandable composite as an actuator layer of the personalized medicinal platform which was triggered by heating the electrodes beneath. Each reservoir was enabled using a bench setup (Keithley 2400C Sourcemeter) or battery based system (CR2032 Lithium Coin Cell Battery). We have different volumes of reservoirs for different drugs. Predetermined portions of the drugs can be mixed by manipulating the reservoirs using a thermally expandable layer. Fluids come from different reservoirs 323 and mix through the microfluidic channels. When the composite expands over the heater, it pushes the fluids outside the reservoir towards the microfluidic channels. Expansion is assumed to be complete when most of the fluids inside the reservoirs are ejected. Water solutions with different colors and different pH values were used to test the system's capabilities (FIGS. 3a-3b). Microfluidic mixing capability of the device was validated both experimentally (FIG. 3c) and through simulation (FIGS. 3d-3e).

As an effort to demonstrate the application of this personalized medicinal platform, an integrated system for wireless and programmable actuation of the heating elements was developed. A driver circuitry was constructed to provide sufficient current for all heating elements to reach a certain temperature (above 85° C.). The schematic of the current driver circuit and details of the operation are provided in FIG. S4 (Supplementary Information) with the testing setup and heating profile results in FIG. S3. Smartphone based operation of the system was also demonstrated using a specific designed app.

We have shown a microfluidics-based wearable medicinal preparation platform to pursue the goal of the adaptive on-demand instantaneous in-situ personalization of medicinal preparation which can have a unique impact on global healthcare. Instead of the "one size fits all" treatment approaches for healthcare issues, the reported portable system can prepare drugs, vitamins, and minerals depending on the needs of the individual. The system successfully demonstrated the drug preparation on demand using an expandable polymer composite to mechanically pump drugs from reservoirs upon triggering a heater electrode underneath. We have also shown the high performance CMOS integrated operation of the personalized medicinal preparation platform with wearable sensors and smartphones to instantaneously respond to one's physiological condition. In the future, the number of reservoirs can be increased to include more drugs and different dosages.

Moreover, drug delivery systems and therapeutic actuators can be integrated to deliver produced drugs, and perform therapeutic actions, respectively.

Extended Experimental Procedures

Thermal Simulations

Table 1 shows the relevant properties of different materials for the thermal simulation and experimental results of the heaters, related to FIG. 1h. $\rho$, cp, $\sigma$, k represent the density, heat capacity at constant pressure, electrical conductivity and thermal conductivity, respectively.

TABLE 1

| Material | $\rho$ (kg/m3) | Cp (J/kg/K) | $\sigma$ (S/m) | k (W/m/K) |
| --- | --- | --- | --- | --- |
| Gold | 19300 | 129 | $7.1e^6$ | 317 |
| Polyimide | 1300 | 1100 | $6.6e^{-16}$ | 0.15 |
| Quartz glass | 2210 | 730 | $1e^{-14}$ | 1.4 |

Laser patterned heater (180 nm thick gold on 125 µm thick polyimide substrate) was adhered to a 1 cm thick quartz glass substrate. The bottom surface of the glass substrate was provided with a constant room temperature (25° C.). The surfaces of the device in contact with the surrounding air undergo natural convection. The relevant properties of the materials used in the heater setup are reported in Table 1. For an input power delivered to the heaters, the three dimensional (3D) finite element analysis (FEA) of the setup was carried out to report the stationary study of the heater temperature distributions, as shown in FIG. 1h. It can be observed that the thermal simulations of the heaters are in good agreement with the experimental results (FIG. 1f). Moreover, from the heat map it can be observed that for any activated heater, the temperature increases to above 80° C. only in the regions around the heater surface. Since, the activation temperature for expandable polymer is 80° C., it is contemplated that only the regions of expandable polymer immediately around the activated heater surface expand, which is experimentally verified by FIG. 2g.

Fluidic Simulations

A 3D FEA was carried out to observe the simultaneous flow of liquids trough the micromixer structure of 100 µm from the channels of reservoirs A and B, respectively. The liquids flowing from reservoirs A and B were water mixed with a yellow colored dye of concentration 30 mol/m$^3$ and water mixed with a blue colored dye of concentration 20 mol/m$^3$, respectively. The density and dynamic viscosity of water were 1000 kg/m$^3$ and 1e$^{-3}$ (Pa·s), respectively. The flow rate at the inlet of the channels of reservoirs, the diffusion coefficient and the pressure at the outlet of the structure were 5e$^{-11}$ m$^3$/s, 4e$^{-10}$ m$^2$/s and 0 Pa, respectively. This resulted in the laminar flow of the liquids through the microfluidic structure. The simulation result for the stationary study of the concentration plot is shown in FIG. 3d. It can be observed that the two liquids are completely mixed around 5th column of the mixer. Moreover, we have varied the flow rate at the input of the channels and observed the complete mixing of fluids at different column numbers, as shown in FIG. 3e. It can be observed that as the flow rate is increased, the complete mixing of fluids occurs at higher column numbers.

Electronics for Wireless and Programmable Actuation of Medicinal Platform

Figure 5:
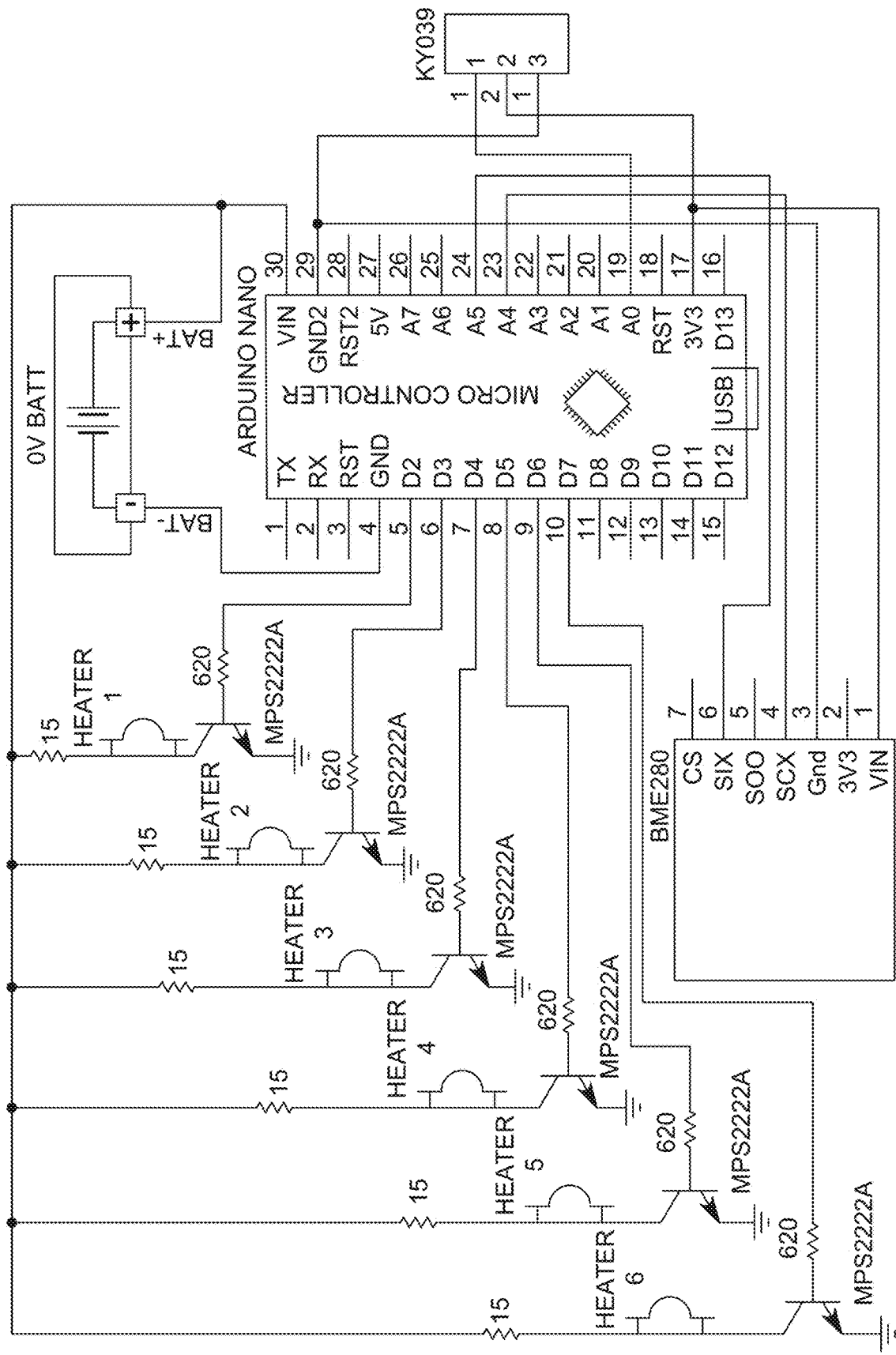
FIG. 5 is a circuit diagram of a control circuit and heating electrodes included in a wearable medicinal platform integrated system in accordance with the present invention, showing an interface between a micro-controller, sensors, and current driver circuitry.
Figure 6A:
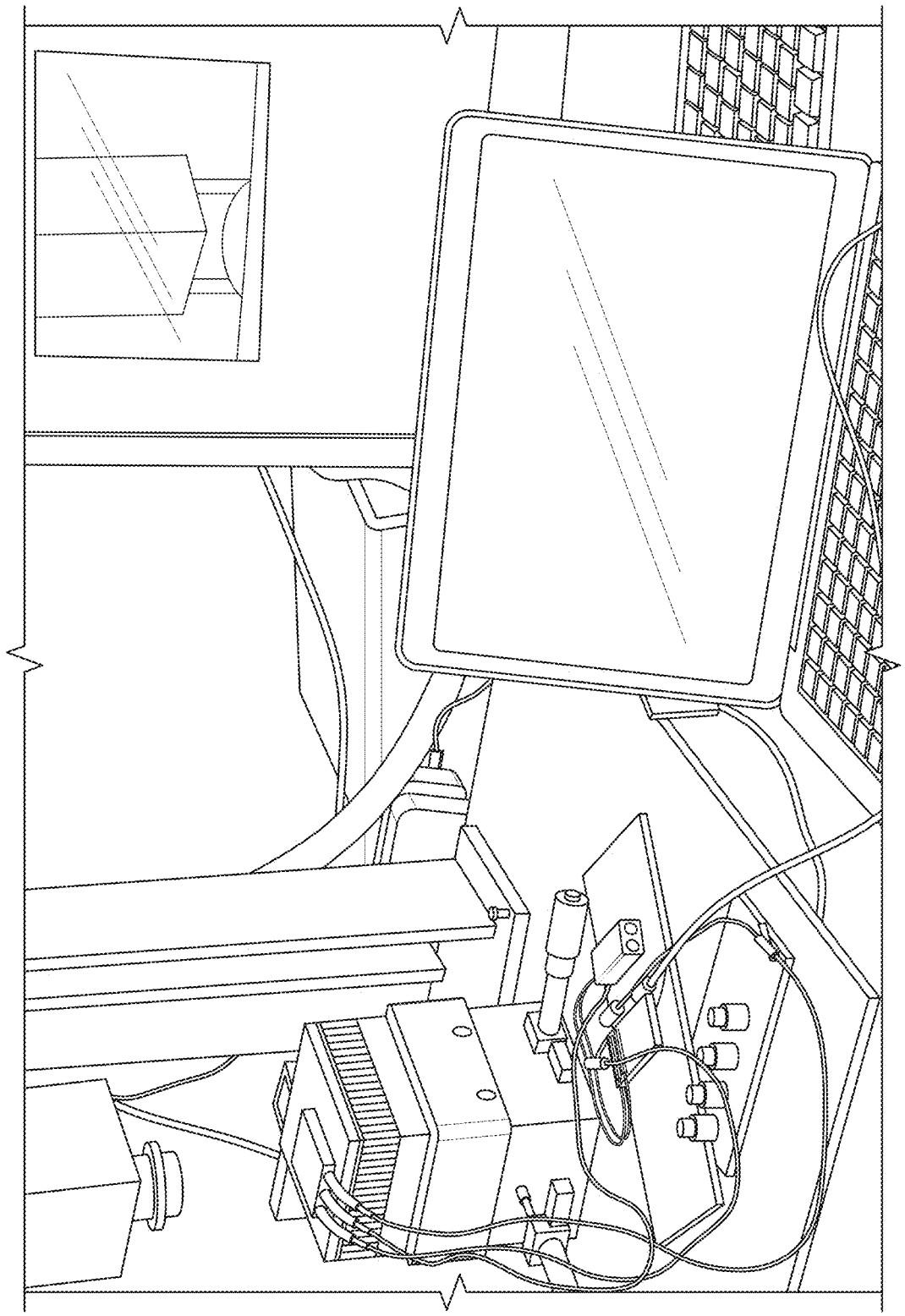
FIG. 6a is a photograph of an integrated system testing environment with a thermal image microscope for real-time temperature analysis of medicinal platform heaters pursuant to the invention.
Figure 6B:
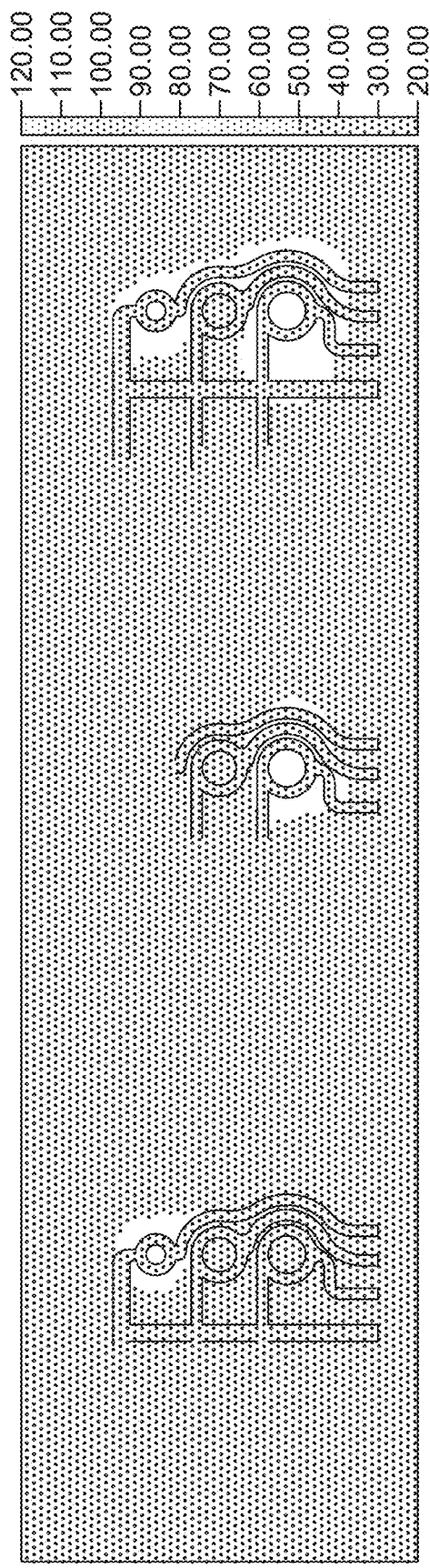
FIG. 6b is an infrared photograph of temperature profiles showing the results of automatically actuated sequential heating (left and middle) and simultaneous heating (right).
Figure 7A:
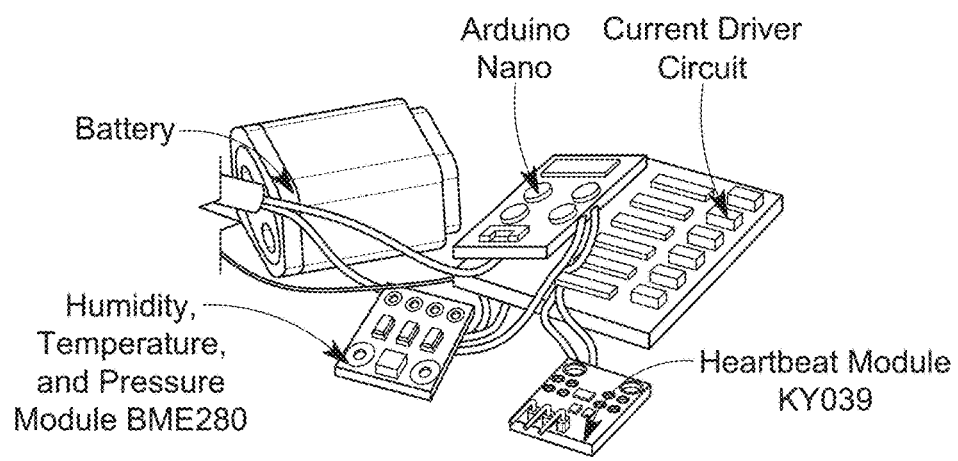
FIG. 7a is a photograph of an integrated system for wearable medicinal platform.
Figure 7B:
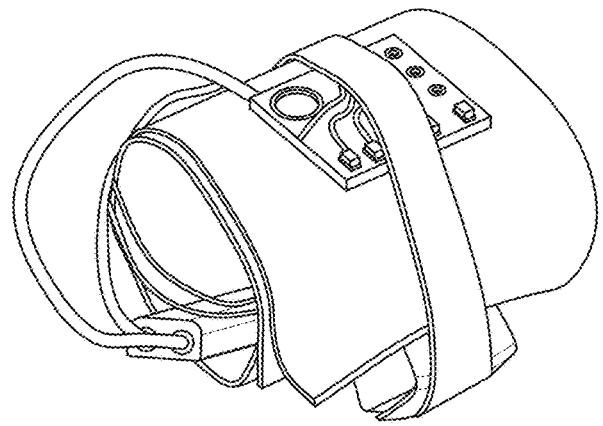
FIG. 7b is a photograph of the integrated system of FIG. 7a placed onto a 3D-printed sleeve.
Figure 7C:
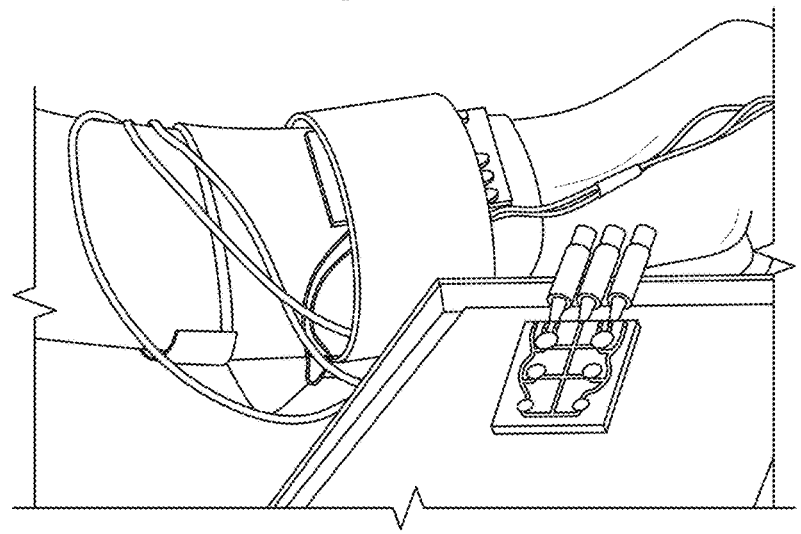
FIG. 7c is a photograph of the wearable system of FIG. 7b on a wrist of a test subject with connections to a medicinal platform in accordance with the present invention, for the real-time fatigue detection test.

As an effort to demonstrate the application of microfluidic medicinal platform, an integrated system for wireless and programmable actuation of the heating elements is developed. A current driver circuitry is constructed to provide sufficient current for all heating elements to reach a certain temperature. A micro-controller provides a mean to programmatically actuate each heater by turning on specific driver transistor. Each driver circuit consists of an NPN BJT with a base resistor; the base resistor acts to limit the bias current flowing to the gate that will ultimately control the current through the collector. A current limiting resistor is also connected in series with each heating element allowing a better control of the maximum current thus temperature generated. The schematic of the current driver circuit is provided in FIG. 5 with the testing setup and heating profile results in FIGS. 6a and 6b. FIG. 7a is a photograph of an integrated system for wearable medicinal platform, FIG. 7b is a photograph of the integrated system of FIG. 7a placed onto a 3D-printed sleeve, and FIG. 7c is a photograph of the wearable system of FIG. 7b on a wrist of a test subject with connections to a medicinal platform for the real-time fatigue detection test. The current flowing across the heater can be found by, $$I_c = (V_{cc} - V_{ce})/(R_c + R_{heater}).$$

After specifying a definite current flowing through the heating element, the base resistor can then be found by substituting the value to, $$I_b = I_c/h_{FE}$$

$$R_b = (V_i - V_{be})/3 * I_b$$

REFERENCES

1 Spear, B. B., Heath-Chiozzi, M. & Huff, J. Clinical application of pharmacogenetics. *Trends Mol. Med.* 7, 201-204 (2001).
2 Abrahams, E. & Silver, M. The case for personalized medicine. *J. Diabetes Sci. Technol.* 3, 680-684 (2009).
3 Chan, I. S. & Ginsburg, G. S. Personalized medicine: progress and promise. *Annu. Rev. Genomics Hum. Genet.* 12, 217-244 (2011).
4 Adamo, A. et al. On-demand continuous-flow production of pharmaceuticals in a compact, reconfigurable system. *Science* 352, 61-67 (2016).
5 Mudanyali, O. et al. Integrated rapid-diagnostic-test reader platform on a cellphone. *Lab Chip* 12, 2678-2686 (2012).
6 Erickson, D. et al. Smartphone technology can be transformative to the deployment of lab on-chip diagnostics. *Lab Chip* 14, 3159-3164 (2014).
7 Oncescu, V., Mancuso, M. & Erickson, D. Cholesterol testing on a smartphone. *Lab Chip* 14, 759-763 (2014).
8 Gao, W. et al. Fully integrated wearable sensor arrays for multiplexed in situ perspiration analysis. *Nature* 529, 509-514 (2016).
9 Choi, M. K. et al. Cephalopod-Inspired Miniaturized Suction Cups for Smart Medical Skin. *Adv. Healthcare Mat.* 5, 80-87 (2016).
10 Honda, W., Harada, S., Arie, T., Akita, S. & Takei, K. Wearable, Human-Interactive, Health-Monitoring, Wireless Devices Fabricated by Macroscale Printing Techniques. *Adv. Functional Mat.* 24, 3299-3304 (2014).
11 Nassar, J. M. et al. Paper Skin Multisensory Platform for Simultaneous Environmental Monitoring. *Adv. Materials Tech.* (2016).
12 Oncescu, V., O'Dell, D. & Erickson, D. Smartphone based health accessory for colorimetric detection of biomarkers in sweat and saliva. *Lab on a Chip* 13, 3232-3238 (2013).
13 Ozcan, A. Mobile phones democratize and cultivate next-generation imaging, diagnostics and measurement tools. *Lab on a chip* 14, 3187-3194 (2014).
14 Spieth, S. et al. An intra-cerebral drug delivery system for freely moving animals. *Biomed. Microdevices* 14, 799-809 (2012).
15 Jeong, J.-W. et al. Wireless optofluidic systems for programmable in vivo pharmacology and optogenetics. *Cell* 162, 662-674 (2015).
16 Samel, B., Griss, P. & Stemme, G. A thermally responsive PDMS composite and its microfluidic applications. *J. Microelectromech. Syst.* 16, 50-57 (2007).
17 Intakes, I. o. M. S. C. o. t. S. E. o. D. R. *Dietary reference intakes for thiamin, riboflavin, niacin, vitamin B6, folate, vitamin B12, pantothenic acid, biotin, and choline*. (National Academies Press (US), 1998).
18 Monsen, E. R. Dietary reference intakes for the antioxidant nutrients: vitamin C, vitamin E, selenium, and carotenoids. *Journal of the American Dietetic Association* 100, 637-640 (2000).
19 Trumbo, P., Yates, A. A., Schlicker, S. & Poos, M. Dietary reference intakes: vitamin A, vitamin K, arsenic, boron, chromium, copper, iodine, iron, manganese, molybdenum, nickel, silicon, vanadium, and zinc. *J. Am. Diet. Assoc.* 101, 294-301 (2001).
20 Lee, C. H. et al. Materials and Wireless Microfluidic Systems for Electronics Capable of Chemical Dissolution on Demand. *Adv. Funct. Mat.* 25, 1338-1343 (2015).
21 Choi, M. K. et al. Cephalopod-Inspired Miniaturized Suction Cups for Smart Medical Skin. *Adv. Healthcare Mater.* 5, 80-87 (2016).
22 Kim, D.-H. et al. Epidermal electronics. *Science* 333, 838-843 (2011).
23 Schwartz, G. 271 et al. Flexible polymer transistors with high pressure sensitivity for application in electronic skin and health monitoring. *Nat. Commun.* 4, 1859 (2013).
24 Farra, R. et al. First-in-human testing of a wirelessly controlled drug delivery microchip. *Sci. Transl. Med.* 4, 122ra121-122ra121 (2012).
25 Roxhed, N. et al. A compact, low-cost microliter-range liquid dispenser based on expandable microspheres. *J. Microelectromech. Syst.* 16, 2740 (2006).

We claim:
1. An apparatus for personal health maintenance, comprising:
   a carrier member;
   at least one sensor attached at least indirectly to the carrier member and configured for measurement of at least one physiological parameter of a user;
   an attachment device connected to the carrier member for maintaining the sensor in operative proximity with the user;
   plural reservoirs provided on the carrier member and each reservoir of the plural reservoirs containing a corresponding preselected composition;
   a dispensing mechanism comprising (1) an expandable polymer composite layer provided as a thin film layer on the carrier member in direct contact with each reservoir in the plural reservoirs, and (2) plural electrodes, each electrode being individually addressed by an electronic processor; and the processor mounted to or carried by the carrier member and operatively connected to the sensor for receiving a signal encoding a measurement of the physiological parameter from the sensor, wherein the processor is configured to determine a divergence of the physiological parameter from a predetermined magnitude, the processor is operatively connected to the plural electrodes of the dispensing mechanism for ejecting, from each reservoir of the plural reservoirs, an amount of the corresponding preselected composition to be mixed with another amount of the preselected composition from another reservoir of the plural reservoirs, to obtain a mixture, and the mixture to be administered to the user to reduce the divergence of the physiological parameter from the predetermined magnitude, wherein the amount of the corresponding preselected composition and the another amount of the preselected composition forming the mixture are determined by the processor adaptively, on-demand, instantaneously, to be in-situ personalized for the user, based on the measurement of the physiological parameter from the sensor, and wherein the physiological parameter is one of a body temperature, a blood pressure, a pulse rate, a skin hydration, a perspiration state, and a respiration rate.

2. The apparatus of claim 1, wherein the expandable polymer composite layer includes gas-filled micro-bubbles or microspheres.

3. The apparatus of claim 2, wherein the dispensing mechanism further includes:
an electric circuit with at least one heating element proximate the expandable polymer composite layer, wherein the at least one heating element includes an electrode of the plural electrodes.

4. The apparatus of claim 1, wherein the plural reservoirs are a part of a microfluidic circuit, which is disposed on a substrate included in the carrier member.

5. The apparatus of claim 4, wherein the dispensing mechanism includes a micro-electrical circuit disposed on the substrate in juxtaposition to the plural reservoirs.

6. The apparatus of claim 5, wherein the dispensing mechanism further includes gas-filled microspheres adjacent the plural reservoirs, the micro-electrical circuit including a heating element juxtaposed to the microspheres.

7. The apparatus of claim 1, wherein the sensor is a temperature sensor, an electrical conductivity or electrical resistance detector, or a pressure sensor.

8. The apparatus of claim 1, wherein the dispensing mechanism includes a nozzle to dispense the amount of the preselected composition into or onto an ingestible substance.

9. The apparatus of claim 1, further comprising:
an alert signal generator operatively connected to the processor for prompting the user to take action to ingest the amount of the preselected composition.

10. A microfluidic dispensing assembly comprising:
a substrate;
first and second reservoirs provided on the substrate and the first and second reservoirs containing first and second preselected compositions, respectively;
a dispensing mechanism provided in juxtaposition to the first and second reservoirs, the dispensing mechanism including (1) an expandable polymer composite layer comprising a thin film layer directly exposed to the first and second reservoirs, and (2) plural electrodes, each electrode being individually addressed by an electronic processor; and the electronic processor operatively connected to the dispensing mechanism for operating the plural electrodes of the dispensing mechanism to eject, from the first and second reservoirs, a mixture including a first amount of the first preselected composition corresponding to the first reservoir and a second amount of the second preselected composition corresponding to the second reservoir, wherein the electronic processor is configured to control the first and second amounts of the first and second preselected compositions, based on a measured physiological parameter of a user, so that a concentration of the mixture is adjustable on-demand, instantaneous, and in-situ personalized for the user, and wherein the physiological parameter is one of a body temperature, a blood pressure, a pulse rate, a skin hydration, a perspiration state, and a respiration rate.

11. The microfluidic dispensing assembly of claim 10, wherein the expandable polymer composite layer includes gas-filled micro-bubbles or microspheres.

12. The microfluidic dispensing assembly of claim 11, wherein the dispensing mechanism further includes an electric circuit with at least one heating element proximate the expandable polymer composite layer, the electronic processor being operatively connected to the electric circuit, and the at least one heating element including an electrode of the plural electrodes.

13. The microfluidic dispensing assembly of claim 10, wherein the first and second reservoirs are part of a microfluidic circuit, which is disposed on the substrate.

14. The microfluidic dispensing assembly of claim 10, further comprising:
a sensor operatively connected to the electronic processor; and
an attachment mechanism for maintaining the sensor in operative engagement with the user,
wherein the electronic processor is configured to receive a signal encoding a measurement of the physiological parameter from the sensor, the electronic processor is configured to determine a divergence of the physiological parameter from a predetermined magnitude, the electronic processor is operatively connected to the dispensing mechanism for ejecting, from the first and second reservoirs, the first and second amounts of the first and second preselected compositions to be administered to the user to reduce the divergence of the physiological parameter from the predetermined magnitude.

15. An apparatus for personal health maintenance, comprising:
a carrier member;
at least one sensor attached at least indirectly to the carrier member and configured for measurement of at least one physiological parameter of a user;
first and second reservoirs provided on the carrier member and the first and second reservoirs containing first and second preselected compositions, respectively;
a dispensing mechanism comprising (1) an expandable polymer composite layer provided as a single thin film layer on the carrier member in direct contact with the first and second reservoirs, and (2) plural electrodes each electrode being individually addressed by an electronic processor; and
the electronic processor operatively connected to the dispensing mechanism for operating the plural electrodes of the dispensing mechanism to eject, from the first and second reservoirs, a mixture including a first amount of the first preselected composition corresponding to the first reservoir and a second amount of the second preselected composition corresponding to the second reservoir, to be administered to the user to reduce a divergence of the physiological parameter from a predetermined magnitude, wherein the electronic processor is configured to control the first and second amounts of the first and second preselected compositions adaptively, on-demand, instantaneously, to be in-situ personalized for the user, based on the measurement of the physiological parameter, which is input from the at least one sensor, and wherein the physiological parameter is one of a body temperature, a blood pressure, a pulse rate, a skin hydration, a perspiration state, and a respiration rate.

16. The apparatus of claim 15, wherein: the expandable polymer composite layer includes gas-filled micro-bubbles or microspheres; and the dispensing mechanism includes an electric circuit with at least one heating element proximate the expandable polymer composite layer and the at least one heating element including an electrode of the plural electrodes.

17. The apparatus of claim 15, wherein the first and second reservoirs are part of a microfluidic circuit disposed on a substrate included in the carrier member.

18. The apparatus of claim 17, wherein the dispensing mechanism includes a micro-electrical circuit disposed on the substrate in juxtaposition to the first and second reservoirs.

19. The apparatus of claim 15, wherein the at least one sensor is a temperature sensor, an electrical conductivity or electrical resistance detector, or a pressure sensor.

* * * * *